United States Patent
Harazin et al.

(10) Patent No.: US 7,387,023 B2
(45) Date of Patent: Jun. 17, 2008

(54) METHOD AND APPARATUS TO REJECT ELECTRICAL INTERFERENCE IN A CAPACITIVE LIQUID LEVEL SENSOR SYSTEM

(75) Inventors: Richard Raymond Harazin, Lombard, IL (US); Ronald Alvin Zweifel, Naperville, IL (US)

(73) Assignee: Perkinelmer LAS, Inc., Waltham, MA (US)

( * ) Notice: Subject to any disclaimer, the term of this patent is extended or adjusted under 35 U.S.C. 154(b) by 0 days.

(21) Appl. No.: 11/706,002

(22) Filed: Feb. 13, 2007

(65) Prior Publication Data

US 2007/0137315 A1 Jun. 21, 2007

Related U.S. Application Data

(62) Division of application No. 10/975,658, filed on Oct. 28, 2004, now Pat. No. 7,191,647.

(60) Provisional application No. 60/481,581, filed on Oct. 30, 2003.

(51) Int. Cl.
*G01F 23/00* (2006.01)
(52) U.S. Cl. .................... 73/290 R; 340/620
(58) Field of Classification Search .............. 73/290 R; 340/620

See application file for complete search history.

(56) References Cited

U.S. PATENT DOCUMENTS 4,326,851 A * 4/1982 Bello et al. ............... 73/304 C (Continued)

FOREIGN PATENT DOCUMENTS

WO WO8401216 3/1984

(Continued)

OTHER PUBLICATIONS

"Industrial Liquid Level Measurement & Control Application Notes," American Magnetics, Inc. http://www.americanmagnetics.com/level/industrial%20applications.html (accessed Nov. 13, 2006).

(Continued)

*Primary Examiner*—Hezron E. Williams
*Assistant Examiner*—Samir M. Shah
(74) *Attorney, Agent, or Firm*—Lowrie, Lando & Anastasi, LLP

(57) ABSTRACT

Methods, systems, and computer program products for measuring a capacitance between a probe and a liquid, pausing movement of the probe based on a rate of change of the capacitance, further measuring the capacitance while the probe is paused, and, based on the further measurements, performing one or more of: resuming movement of the probe, determining a position of the probe, aspirating liquid into the probe, and dispensing from the probe. Resuming movement of the probe can include returning iteratively to measuring a capacitance, and the further measuring can be performed for a time interval that can vary based on the further measured capacitance(s), a probe movement characteristic, and/or a sampling rate.

12 Claims, 5 Drawing Sheets

U.S. PATENT DOCUMENTS

| | | | |
|---|---|---|---|
| 4,977,786 A * | 12/1990 | Davis | 73/864.24 |
| 5,027,075 A * | 6/1991 | Harding, Jr. | 324/662 |
| 5,049,826 A | 9/1991 | Sasao | |
| 5,365,783 A * | 11/1994 | Zweifel | 73/304 C |
| 5,627,522 A * | 5/1997 | Walker et al. | 340/618 |
| 5,855,851 A * | 1/1999 | Matsubara et al. | 422/100 |
| 6,328,934 B1 * | 12/2001 | Ljung et al. | 422/119 |
| 7,191,647 B2 | 3/2007 | Harazin | |

FOREIGN PATENT DOCUMENTS

| WO | WO9217761 | 10/1992 |
|---|---|---|
| WO | WO2005-045635 A2 | 5/2005 |

OTHER PUBLICATIONS

"The Designing and Application of the Helium Liquid-Level Capacitance Probe." Ryan D. Swain, Alabama A&M University, 1996. sist.fnal.gov/archive/96-topics/papers/Ryan_Swain/ResearchP.doc (accessed Nov. 13, 2006).

International Search Report for WO2005-45635 (listed as WO2005-45635A3).

Supplemental Search Report for EP Application No. 04796734.4.

* cited by examiner

METHOD AND APPARATUS TO REJECT ELECTRICAL INTERFERENCE IN A CAPACITIVE LIQUID LEVEL SENSOR SYSTEM

PRIORITY CLAIM

The present application is a divisional of U.S. application for patent Ser. No. 10/975,658 filed Oct. 28, 2004, now U.S. Pat. No. 7,191,647, which claims priority from U.S. Provisional Application for Patent Ser. No. 60/481,581, filed Oct. 30, 2003, and entitled "Method and Apparatus to Reject Electrical Interference in a Capacitive Liquid Level Sensor System" by Richard R. Harazin and Ronald A. Zweifel, the disclosures of which are hereby incorporated by reference in their entireties.

BACKGROUND

1. Technical Field

The present application relates to liquid level sensor systems. More specifically, the present application relates to the rejection of interference which adversely affects the operation of a capacitive liquid level sensor (LLS) system.

2. Description of Related Art

Withdrawing and dispensing precise volumes of a liquid without contaminating the liquid is an important part of many clinical applications and laboratory tests. While attempts to address these needs manually have failed to provide the needed accuracy and purity, a number of automated or semi-automated liquid-measuring systems are presently being used to gauge more precisely the small liquid volumes that need to be withdrawn and/or dispensed.

One of the more popular types of liquid-measuring systems uses a motor-controlled pipette-like probe to aspirate or dispense a desired amount of fluid from or into a container. The probe is movably mounted over the container and, using a precision-controlled motor, is vertically (z-axis) lowered into the container until the tip of the probe reaches a desired level below or above the upper surface of the liquid (the meniscus). A desired amount of liquid is then withdrawn from or dispensed into the container. Such systems have been designed to: minimize/reduce cross-contamination between the contents of different containers, avoid splashing of the liquid during the aspiration (or deposition) process, and minimize/reduce the portion of the probe that must be washed.

In many instances, the automated or semi-automated liquid-measuring system does not know beforehand the level of fluid contained within the container. Nonetheless, the pipette-like probe must be lowered to a certain position with the expectation that the probe has been precisely positioned with respect to the fluid level. Several systems control the position of the probe tip without previously knowing the upper level of the liquid in the container by sensing for the upper level of the liquid in the container as the probe is being lowered. For example, a measurement can be made of some electrical phenomena associated with a change in the capacitance between the probe and the liquid in the container as the tip of the probe approaches the liquid. This measurement may identify a liquid sense event (for example, penetrating the meniscus or withdrawing from the meniscus) when the capacitance between the probe and the liquid reflects a change in voltage level that is greater than a threshold reference level.

A well known system and technique for capacitive-based sensing of liquid level in a z-axis controlled liquid-measuring system is taught by U.S. Pat. No. 5,365,783, to Ronald A. Zweifel (the "Zweifel system"), the disclosure of which is hereby incorporated by reference.

In some existing systems, the labware can collect and store static electricity. As the probe is moved closer and closer to the container, one or more static discharge events may occur between the probe and container during probe movement. These static discharge events can cause an instantaneous change in a signal indicative of the measured capacitance which can incorrectly be detected by the system as a liquid event (for example, a false positive indication that the probe is in the liquid when in fact it is still positioned above the liquid). Second, the laboratories where these systems are commonly used are typically illuminated using fluorescent light fixtures. The electronic ballasts used by such fixtures emit high frequency electromagnetic radiation. Probes can thus act as an antenna with respect to such radiation, and the corresponding noise signal from that antenna-captured radiation can adversely affect a signal indicative of the measured capacitance and can cause an incorrect detection of a liquid event.

SUMMARY

An embodiment of the present teachings processes a signal indicative of a capacitance formed between a probe that is controlled to move into and/or out of a container and a liquid contained within the container. The capacitance indicative signal can be filtered to produce a trigger signal indicative of an event with respect to probe movement. The trigger signal is also processed to detect occurrence of the event and movement of the probe is paused in response to a detected event occurrence.

Another embodiment also processes a signal indicative of a capacitance formed between a probe that is controlled to move into and/or out of a container and a liquid contained within the container. The capacitance indicative signal can be low pass filtered to attenuate high frequency noise and produce a filtered capacitance indicative signal. The filtered signal can be high pass filtered to attenuate low frequency components and produce a trigger signal indicative of an event with respect to probe movement. The trigger signal is then processed to detect occurrence of the event and the filtered capacitance indicative signal is processed to determine whether the event is an interference event or a liquid sensing event.

In accordance with an embodiment, a liquid-measuring system includes a probe that is controlled to move into and out of a container containing a liquid, where a capacitance forms between the probe and the liquid. A capacitive sensing system coupled to the probe generates a signal indicative of the capacitance. A control system that receives the capacitance indicative signal responds to an event-related change therein by pausing the movement of the probe and further evaluating the capacitance indicative signal while probe movement is paused to determine whether the change was caused by an interference event or a liquid sensing event.

In one embodiment, a liquid-measuring system includes a probe that is controlled to move into and/or out of a container containing a liquid, where a capacitance can be detected that is indicative of a capacitance between the probe and the liquid. A capacitive sensing system coupled to the probe generates a signal indicative of the capacitance. A control system receives the capacitance indicative signal, filters the capacitance indicative signal and processes the filtered capacitance indicative signal to determine whether a change in the capacitance indicative signal was caused by an interference event or a liquid sensing event.

The present teachings thus include a liquid-level sensing system having a probe that is controlled to move into and/or out of contact with a liquid, a capacitive sensing system coupled to the probe to generate a signal indicative of a capacitance between the probe and the liquid, and a control system that receives the capacitance indicative signal, and based thereon, pauses the movement of the probe and processes the capacitance indicative signal while probe movement is paused to determine whether the probe moved at least one of into and out of contact with the liquid. The control system can pause the movement of the probe based on a rate of change of a signal based on the capacitance indicative signal. The control system can process the capacitive indicative signal while the probe movement is paused to determine that changes in the capacitance indicative signal are based on signal interference, such as, for example, high frequency noise, static discharge, etc. In an embodiment, the capacitance indicative signal is a voltage signal.

The control system can include a bandpass filter operable on the capacitance indicative signal to generate a trigger signal, and movement of the probe is paused based on the trigger signal, for example, when the trigger signal exceeds a threshold.

The methods, systems, and computer program products presented herein include a liquid-measuring system that includes a probe that is controlled to move at least one of into and out of contact with a liquid, a capacitive sensing system coupled to the probe to generate a signal indicative of a capacitance between the probe and the liquid, and a control system that receives the capacitance indicative signal, filters the capacitance indicative signal, and processes the filtered capacitance indicative signal to determine whether a change in the capacitance indicative signal was caused by probe movement into and/or out of contact with the liquid.

In an embodiment, the present teachings include a system for processing a signal indicative of a capacitance formed between a probe that is controlled to move into and/or out of contact with a liquid, and the liquid, where the system includes a low pass filter that operates on the capacitance indicative signal to produce a filtered capacitance indicative signal, a high pass filter that operates on the filtered capacitance indicative signal to produce a trigger signal indicative of an event with respect to probe movement, and processor instructions operable on the filtered capacitance indicative signal and trigger signal, where the instructions detect occurrence of the event from the trigger signal and the instructions determine, based on the filtered capacitance signal, whether the event is a liquid sensing event. The processor instructions can pause the movement of the probe in response to a detected event occurrence, and can process the filtered capacitance indicative signal while probe movement is paused to determine whether the detected event occurrence is an interference event or a liquid sensing event. The processor instructions can thus restart and/or resume movement of the probe if the detected event occurrence is determined to be an interference event.

The teachings include a method for processing a signal indicative of a capacitance formed between a probe that is controlled to move into and/or out of contact with a liquid, and the liquid, including low pass filtering the capacitance indicative signal to produce a filtered capacitance indicative signal, high pass filtering the filtered capacitance indicative signal to produce a trigger signal indicative of an event with respect to probe movement, processing the trigger signal to detect occurrence of the event, and processing the filtered capacitance indicative signal to determine whether the event is a liquid sensing event. Also included is a restarting of movement of the probe if the detected event occurrence is determined to be an interference event.

Accordingly, in an embodiment, the teachings include a system for processing a signal indicative of a capacitance between a probe that is controlled to move into and/or out of contact with a liquid, and the liquid, the system including a bandpass filter operable on the capacitance indicative signal to produce a trigger signal indicative of an event with respect to probe movement, and a processor having instructions operable on the trigger signal to detect occurrence of the event from processing of the trigger signal and to pause the movement of the probe in response to a detected event occurrence.

In an embodiment, the teachings include a method for processing a signal indicative of a capacitance formed between a probe that is controlled to move into and out of contact with a liquid, and the liquid, including filtering the capacitance indicative signal to produce a trigger signal indicative of an event with respect to probe movement; processing the trigger signal to detect occurrence of the event; and pausing the movement of the probe in response to a detected event occurrence. The filtering can include high pass filtering and/or low pass filtering. Processing the trigger signal includes detecting when a trigger signal exceeds a threshold. Pausing the movement of the probe includes processing the filtered capacitance indicative signal after pausing the movement, and, based on the processing, determining whether the event is associated with movement of the probe into contact with the liquid, and/or movement of the probe out of contact with the liquid. The determining also includes determining that the event is not associated with movement of the probe into contact with the liquid and/or movement of the probe out of contact with the liquid, and resuming movement of the probe. Accordingly, the determining can include determining that the event is associated with movement of the probe into contact with the liquid and/or movement of the probe out of contact with the liquid, and determining a level of the fluid based on the position of the probe and/or a sensor associated with the probe.

In one embodiment, the teachings include measuring a capacitance between a probe and a liquid, pausing movement of the probe based on a rate of change in the capacitance, further measuring the capacitance while the probe is paused, and, based on the further measurements, performing one or more of: resuming movement of the probe, determining a position of the probe, aspirating liquid into the probe, and, dispensing from the probe. Resuming movement of the probe includes a method that includes returning iteratively to measuring a capacitance. The further measuring can be performed for a time interval that can be based on predetermined time interval, and/or based on the further measured capacitance. In further measuring, the method can include comparing data based on the further measurements to at least one threshold, changing a counter value based on the comparisons, and, determining the time interval based on the changed counter value. The further measuring can be based on a sampling interval and/or a probe movement characteristic that can include a probe speed, a probe velocity, and a probe acceleration, for example.

BRIEF DESCRIPTION OF THE DRAWINGS

A more complete understanding of the present teachings may be acquired by reference to the following Detailed Description when taken in conjunction with the accompanying Drawings wherein.

DETAILED DESCRIPTION OF THE DRAWINGS

Figure 1:
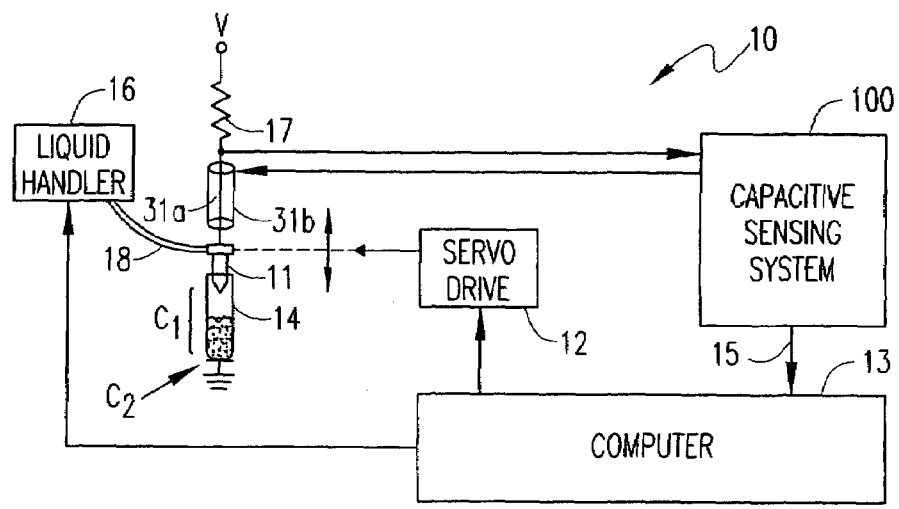
FIG. 1 is a block diagram of a z-axis controlled automated liquid-measuring system.

FIG. 1 illustrates a z-axis controlled automated liquid-measuring system 10 which provides control over the position of a probe 11 with respect to an unknown level of liquid in a conventional laboratory container 14. Movement of the probe 11 in the z-axis into or out of the container 14 is controlled by a conventional servo-drive 12 which is controlled by a microcomputer or CPU 13. The CPU 13 determines the position of the probe 11 with respect to the level of the liquid in the container 14 by monitoring a signal 15 representing capacitance between: the probe 11 and the liquid in the container 14, the liquid in the container 14, and ground. The CPU may also be programmed to control a liquid handler 16 (e.g., syringe) which can aspirate or dispense a desired amount of fluid from or into the container 14 through the probe 11 via a flexible tube 18 made from a chemically inert material such as Teflon, for example.

The stray capacitance, depicted as $C_1$, between the probe 11 and the liquid in the container 14 slowly increases as the probe 11 is moved toward the liquid. When the probe contacts the liquid in the container 14, the stray capacitance, $C_1$, changes virtually instantaneously. A capacitive sensing system 100 is coupled, via a conductor 31a to detect changes in this stray capacitance, and provide corresponding sensor data to the CPU 13 in the form of signal 15 which is indicative of a capacitance between the probe 11, the liquid in the container 14, and ground.

The stray capacitance $C_1$ is monitored by the system 100 through a sampling operation that with each sample instant applies a voltage to the probe 11/container 14 (i.e., to the capacitance $C_1$) and measures the voltage charge on the capacitance $C_1$ to detect and latch a peak voltage developed on the capacitance $C_1$. This latched peak voltage is output as the signal 15 for application to the CPU 13. In embodiments, the signal 15 is a digital signal representation of the sampled peak voltage value. When the probe 11 contacts the liquid in the container 14, a rapid change occurs in the stray capacitance which causes the measured voltage developed on the capacitance to decrease rapidly. This decreased voltage signal level is detectable in the output signal 15 and does not change for as long as the probe 11 remains in the liquid (assuming no evaporation/loss of liquid).

As an example, at the start of each sampling cycle, the voltage at probe 11 is initially held at 0 Volts via a closed switch (not shown) between ground and conductor 31a. Next, the switch is opened so that the illustrated voltage (e.g. 24V) is applied through an impedance 17 to the capacitance $C_1$. The impedance 17 and the capacitance $C_1$ form an RC time constant such that the voltage at the probe 11 increases at a rate proportional to the capacitance $C_1$. After a fixed time (e.g., approximately 10 microseconds), the peak voltage at probe 11 is measured by the system 100 via conductor 31a. This voltage measurement is indicative of capacitance $C_1$ and is sent to the computer 13 via signal 15. The switch is then closed, thus discharging the capacitance $C_1$ and resetting the voltage at probe 11 to 0 Volts. The foregoing cycle can be continuously repeated at a fixed frequency.

Conductor 31a can be implemented as the inner conductor of a coaxial cable. Conductor 31b can be the shield of the coaxial cable which can be electronically driven at the same voltage as conductor 31a (thus providing near 0 capacitance between the conductor 31a and shield 31b) to reduce changes in cable capacitance (e.g. when the cable is moved or comes in contact with an object), and to reduce external electronic noise.

The capacitive sensing system 100 may be configured in a number of ways to generate the output signal 15 representing the peak voltage charge at the capacitance $C_1$. One exemplary circuit for implementing the capacitive sensing system is taught by U.S. Pat. No. 5,365,783, to Ronald A. Zweifel, the disclosure of which is hereby incorporated by reference.

As the probe is moved toward (or away) from the liquid, the capacitance $C_1$ changes and thus the peak voltage charge storable on the capacitance $C_1$ at each sampling instant also changes. The storable peak voltage charge (provided in the signal 15) is monitored and when it changes (e.g., decreases) at a rate exceeding a rate expected for probe movement, provides an indication of the occurrence of an event such as a liquid level sense event when the probe 11 penetrates the meniscus of the fluid within the container. However, it is known that electromagnetic interference can cause momentary increases/decreases in the storable peak voltage charge where no meniscus penetration has occurred. In such situations, the rate of voltage change (e.g., decrease) which is detected by the capacitive sensing system could be processed by the computer 13 and incorrectly identified as a liquid level sense event (i.e., a false positive indication).

Figure 2:
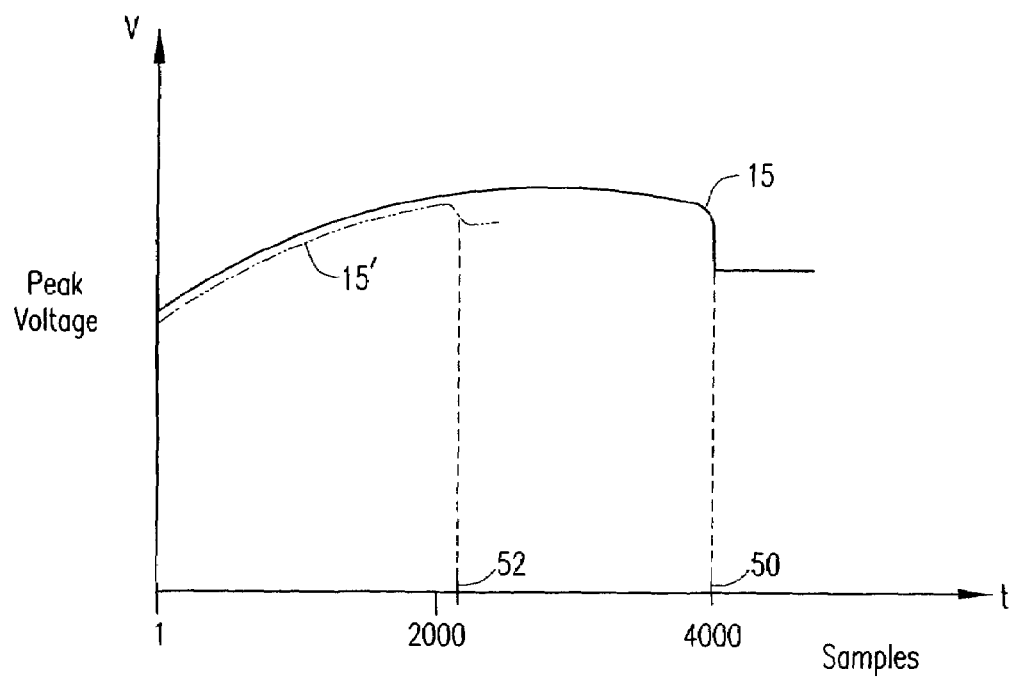
FIG. 2 is a graph illustrating over time a capacitive sensing system output signal as a probe moves towards and then contacts the meniscus of a liquid in a container.

Reference is now additionally made to FIG. 2 wherein there is shown a graph illustrating over time the capacitive sensing system 100 output signal 15 as the probe moves towards and then contacts the meniscus of a liquid in the container 14. The output signal 15 is a digital signal representation of the sampled peak voltage value developed on the capacitance $C_1$. The y-axis of the graph accordingly measures the digitized sampled peak voltage value. The x-axis measures time in terms of a number of samples, wherein the time between sampling instants could, for example, be 500 μsec. The graph shows the output signal 15 peak voltage value generally rising with time as the probe 11 is moved by the servo-drive 12 into the container 14 closer and closer to the meniscus of the contained fluid. When the probe 11 touches the meniscus and penetrates into the fluid contained within the container 14 (at about the sampling instance identified by reference 50), the measured peak voltage at the capacitance $C_1$ decreases virtually instantaneously as evidenced by the voltage drop (voltage step) in output signal 15. The computer 13 detects this rate of change in voltage in the received output signal 15 and provides a control signal to the servo drive 12 to suspend movement of the probe 11 in the z-axis since the probe has penetrated the meniscus of the fluid contained within the container. The computer 13 may further provide a control to the liquid handler 16 to aspirate or dispense a desired amount of fluid from or into the container 14 through the probe 11.

FIG. 2 further shows an output signal 15' that has been perturbed (see, at about the sampling instance identified by reference 52) by interference. For example, the interference-related perturbation could be caused by a static discharge event occurring between the probe and container (or some other dynamic interference event). The interference-related perturbation could additionally and/or optionally be caused by probe 11 receipt of high frequency electromagnetic radiation (e.g., emitted by fluorescent lighting fixtures) that is impressed upon the peak voltage measurement (or some other steady state interference event). In either situation, the interference can cause the measured peak voltage at the capacitance $C_1$ to decrease and thus produce a voltage drop in output signal 15'. In some instances, this voltage drop possesses, at least over a certain number of sampling instants, the characteristics of a voltage step. The computer 13 accordingly could detect this step-like voltage drop in the received output signal 15', and then incorrectly interpret it as an indication that the probe 11 has reached the meniscus. Responsive thereto, the computer would incorrectly provide control/instructions to the servo drive 12 to terminate further movement of the probe 11 in the z-axis. This false positive meniscus detection, however, can result in the probe 11 being incorrectly positioned in the z-axis within the container 14 with respect to the contained liquid. At this position, a proper fluid aspiration or deposition process using the liquid handler 16 cannot be accomplished.

Figure 3:
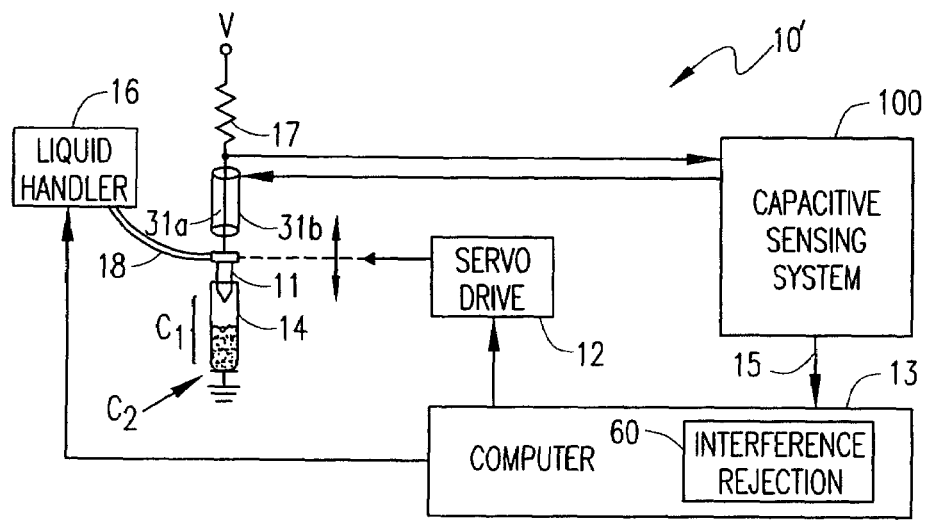
FIG. 3 is a block diagram of a z-axis controlled automated liquid-measuring system in accordance with an embodiment of the present teachings.

Reference is now made to FIG. 3 wherein there is shown a block diagram of a z-axis controlled automated liquid-measuring system 10', in accordance with an embodiment of the present teachings, for controlling a single probe with respect to liquid in a laboratory container. Like reference numbers in FIG. 3 refer to like or similar parts in FIG. 1, the description of which will not be repeated.

Figure 4:
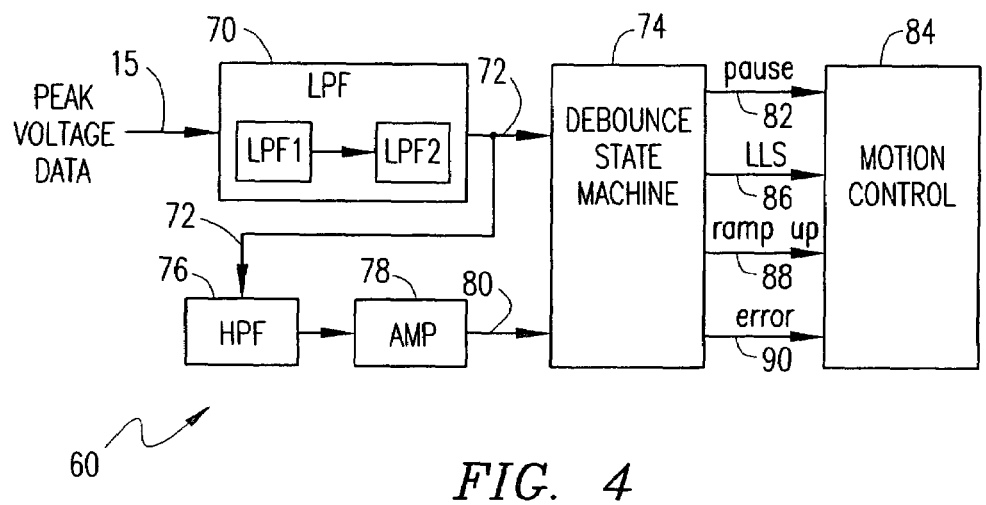
FIG. 4 is a block diagram of an interference rejection processing scheme used by a system according to FIG. 3.

The system 10' of FIG. 3 differs from the system 10 of FIG. 1 in that the computer 13 implements an interference rejection instructions 60 to address dynamic (e.g., static discharge) and steady state (e.g., electromagnetic radiation) interference events. A block diagram of the interference rejection instructions 60 are illustrated in FIG. 4.

A digital low pass filter (LPF) 70 processes the digitized sampled peak voltage value developed on the capacitance $C_1$ to provide low pass filtered data 72. The LPF 70 can be implemented as a series of two digital low pass filters for the reasons discussed herein. The operation of the LPF 70 effectively reduces periodic electromagnetic interference (EMI) which may be present in the received peak voltage data signal 15. Thus, the LPF 70 attenuates high frequency signal components from the signal 15 such as the steady state noise which may be captured by the probe 11 from external radiation sources such as fluorescent light fixtures.

The two series-connected digital low pass filters are based on a bilateral Z transform. The formula used for each of LPF1 and LPF2 is as follows:

$$LPF_n = LPF_{n-1} + ((NEW\ DATA_n - LPF_{n-1})/TAU)$$

where:

LPF$_n$ is the current low pass filter output value;
LPF$_{n-1}$ is the previous low pass filter output value;
NEW DATA$_n$ is the current input value (signal 15); and
TAU is the time constant (as TAU gets larger, F3 db (the cutoff frequency) gets lower).

By routing the output of one filter (LPF1) as an input to a second filter (LPF2), a 2 pole LPF 70 can be formed to increase the cutoff slope (e.g., 12 db per octave instead of 6 db per octave) to provide better noise rejection above F3 db. TAU for each filter stage may be chosen in view of the probe movement speed (e.g., 100 mm/sec), a sample rate, and a specified penetration distance prior to stopping (e.g., no more than 1 mm penetration into the sample). Empirical methods can be used to determine TAU, where generally, in the illustrated embodiments, larger-valued TAU correspond to delayed response. As a example, LPF1 may have TAU=4 and provide a f3 db of 100 Hz, while LPF2 may have TAU=8 and provide a F3 db of 40 Hz.

The low pass filtered output data 72 is applied to a "debounce" state machine 74, and also into a digital high pass filter (HPF) 76. The combination of the LPF 70 and HPF 76 creates a bandpass filter. Bandpass filtering of the received peak voltage data signal 15 generates a "trigger" signal 80 that is amplified by amplifier 78 and applied to the debounce state machine 74.

The digital HPF 76 is created using subtraction, the formula being:

$$HPF_n = LPF_n - LPF_{n-3}$$

where:

HPF$_n$ is the high pass filter output;
LPF$_n$ is the current output value from the second low pass filter; and
LPF$_{n-3}$ is the 3rd previous output value from the second low pass filter.

As an example, the f3 db (cutoff frequency) for the HPF 76 is set at about 80 Hz.

The net effect of running the LPF output data 72 into the HPF is to create an overall bandpass filter effect with a center frequency of about 90 Hz. The amplifier 78 applies a gain of 4 to the HPF output data (the "trigger" signal 80). The gain value, however, is user-selectable and can be adjusted as for compatibility with debounce state machine 74 operations such as threshold comparing of the trigger signal 80 in order to detect that an event has occurred.

Upon detection of a trigger 80 signifying that an event has occurred, the debounce state machine 74 generates a pause control signal 82 which is sent to a motion control process 84 within the computer. Responsive thereto, the motion control process 84 signals the servo drive 12 to momentarily (at least) pause probe 11 movement. With the probe 11 movement paused, the debounce state machine 74 then analyzes a large portion (i.e., multiple sample points) of subsequent LPF output data 72 to determine whether a voltage step in the signal 15 has occurred (see, FIG. 2, reference 50) that is indicative of a liquid event such as penetration of the liquid meniscus within the container, or if instead a perturbation in the signal 15 has occurred (see, FIG. 2, reference 52) that is indicative of interference or noise where liquid penetration position has not yet been reached. For example, in the situation where the event is a static discharge event, pausing of probe 11 movement is beneficial as it allows for the static interference to dissipate. If the event is determined to be a liquid event (because the subsequent multiple sample points of the LPF output data 72 show a voltage step), then the debounce state machine 74 sets a liquid level sense (LLS) flag 86 to true. The setting of this flag indicates to the computer 13 that the probe 11 has penetrated the meniscus of the liquid within the container 14. Responsive thereto, the computer 13 may signal the liquid handler 16 to aspirate or dispense a desired amount of fluid from or into the container 14 through the probe 11. If, on the other hand, the event is determined to be noise (because the subsequent multiple sample points of the LPF output data 72 fail to show a voltage step), the event is rejected by the debounce state machine 74 and a "ramp up" command 88 is issued. Responsive thereto, the motion control process 84 signals the servo drive 12 to continue probe 11 movement in the z-axis (and/or some other axis) in the search for liquid. If the analysis of the multiple sample points of the LPF output data 72 by the debounce state machine 74 is inconclusive with respect to identifying the event (e.g., too much noise to make a decision), and thus probe movement has been paused for too long a period of time, the debounce state machine 74 reports a "liquid not found" error 90.

Figure 5:
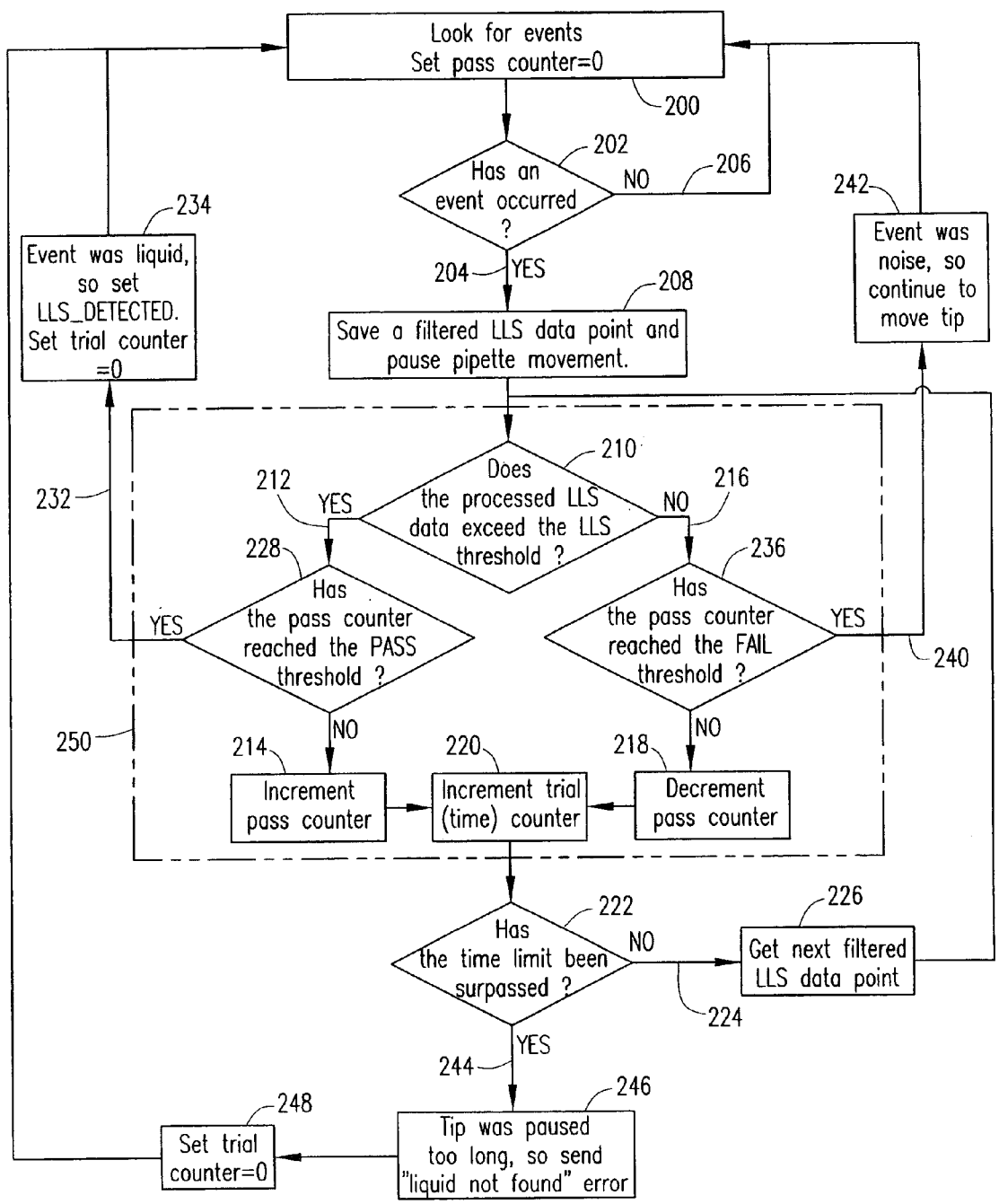
FIG. 5 is a flow chart that diagrams operation of one "DEBOUNCE STATE MACHINE" as shown in FIG. 4.

Reference is now made to FIG. 5 wherein there is shown a flow diagram illustrating logical operations performed by one embodiment of a debounce state machine 74. As discussed above, one purpose of this machine is to determine whether an event is a liquid sense event, or another event such as a noise/interference event. The process for discriminating between a liquid sense event and a noise/interference event will now be explained.

The trigger signal 80 is compared to a user defined liquid level sense (LLS) threshold (200 and 202). If the signal 80 exceeds the LLS threshold, then an "event" is said to have occurred (path 204). If the signal does not exceed the LLS threshold, the process of 200 and 202 is repeated for another sample point (path 206). As an example, this comparison operation can determine whether the signal 80 drops below a certain value point (the threshold), or alternatively whether a magnitude of change in the signal 80 over a given number of samples exceeds the threshold. Other comparisons for event determination based on signal 80 value could also be used.

If the test for an event has been satisfied, in 208 the LPF output data 72 for the sample point immediately preceding the detected event is saved, and a pause control signal 82 is generated and sent to the motion control process 84 to pause probe 11 movement. For example, the z-axis motor in the servo drive 12 may be paused by setting the motor state to "paused".

At 210, the current sample point of the LPF output data 72 is compared to the saved LPF output data 72 sample point (from 208). If the difference between the current LPF output data 72 sample and the saved LPF output data 72 sample point (from 208) exceeds the LLS threshold (path 212), a pass counter is incremented 214. Otherwise (path 216), the pass counter is decremented 218. In either case, a trial (time) counter is incremented 220. This trial (time) counter is then compared 222 with a time limit. If the time limit (e.g., one second) has not been exceeded (path 224), a next current LPF output data 72 sample is obtained 226 and the process returns to 210 to compare that current LPF output data 72 sample to the saved LPF output data 72 sample point (from 208). In this way, the process iterates, while the probe movement is paused, and evaluates subsequent new samples of signal 72 as the process attempts to discern whether the detected event is a liquid event or, for example, noise/interference.

Although the process of FIG. 5 shows the use of the same LLS threshold value for both the event test of 200 and 202 and the voltage test of 210, it will be understood that these thresholds are user definable and may, if desired, be set to different values. Altering of the threshold values affects the sensitivity of the process to detect events and voltage indicative of a liquid sense event. As an example, in an embodiment with a sampling rate of 2 KHz, a user may set the pass threshold to one-hundred, and the fail threshold to negative one-hundred, although such example is provided for illustration and not limitation.

To determine whether the event is a liquid event, the path 212 includes a test 228 where the pass counter is compared to a user defined PASS threshold. If, after looping through/iterating and evaluating subsequent samples, the pass counter has not equaled and/or surpassed the PASS threshold, the loop process continues with the incrementing of the pass counter 214, the testing of the trial (time) counter 220 and 222, and the acquisition of the next current LPF output data 72 sample 226. However, if the pass counter has equaled and/or surpassed the PASS threshold (path 232), the scheme concludes that it has found a liquid event and in 234, the debounce state machine 74 sets the liquid level sense (LLS) flag 86 to true, indicating to the computer 13 that the probe 11 has penetrated the meniscus of the liquid within the container 14. At 234, the trial (time) counter is further reset.

To determine whether the event is a noise/interference event, the path 216 includes a test 236 where the pass counter is compared to a user defined FAIL threshold. If, again after looping through/iterating and evaluating subsequent samples, the pass counter has not reached the FAIL threshold, the loop process continues with the decrementing of the pass counter 218, the testing of the trial (time) counter 220 and 222, and the acquisition of the next current LPF output data 72 sample 226. However, if the pass counter has equaled and/or surpassed the FAIL threshold (path 240), the process concludes it has found a noise event and in 242, the debounce state machine 74 rejects the event and issues a "ramp up" command 88 ordering the computer 13 to signal the servo drive 12 to resume/continue probe 11 movement in the z-axis in the search for liquid.

If the testing of the trial (time) counter in 222 indicates that the time limit has been passed (path 244), this indicates that the analysis of the multiple sample points of the LPF output data 72 by the debounce state machine 74 is inconclusive with respect to identifying the event (perhaps because there is too much noise in the signal to make a decision). In 246, the debounce state machine 74 concludes that probe movement has been paused for too long a period of time without being able to come to an event-type conclusion, and then reports the "liquid not found" error 90. In 248, the trial (time) counter is reset.

It will be recognized by those skilled in the art that the process performed within the box 250 (comprising 212-220, 228-230 and 236-238) in essence integrates the PASS/FAIL threshold data with respect to the comparison of the plurality of loop collected current LPF output data 72 samples to the saved LPF output data 72 sample point (from 208) in order to reach a decision as to whether the event is a liquid event or noise/interference. The integration operation helps reduce (i.e., debounce) noise that may occur while the data is being analyzed.

Figure 6:
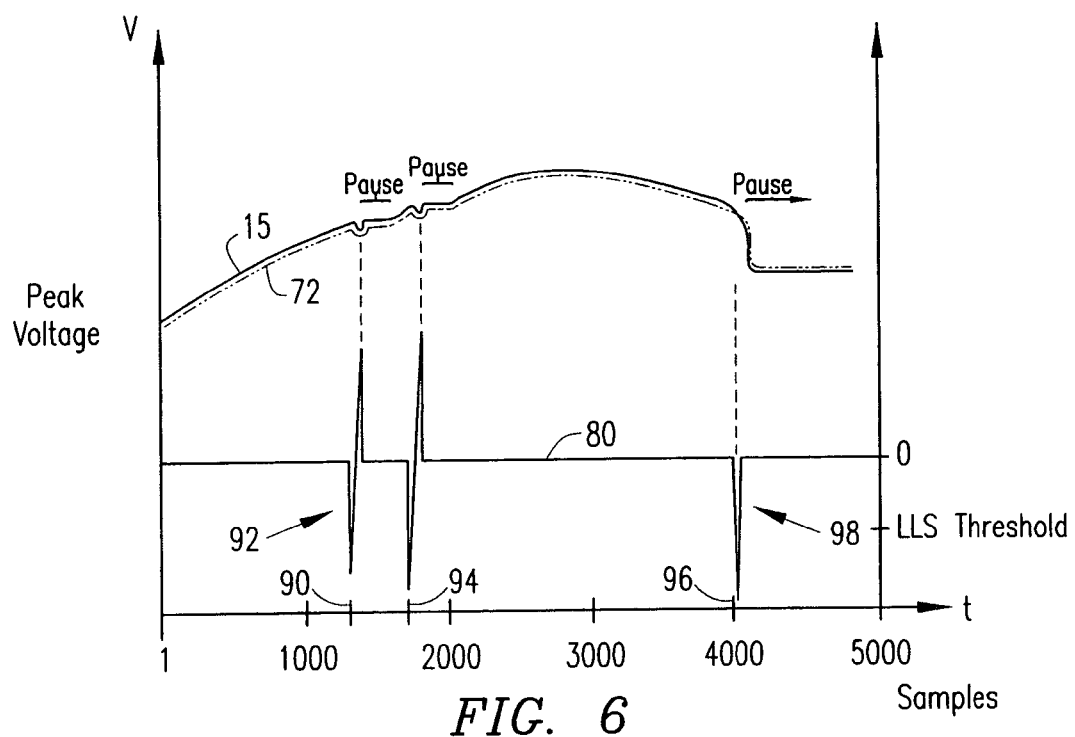
FIG. 6 is a graph illustrating over time a capacitive sensing system output signal, a low pass filtered signal and a bandpass (trigger) signal as a probe moves towards and then contacts the meniscus of a liquid in a container in presence of two static discharge events.

Reference is now made to FIG. 6 wherein there is shown a graph illustrating over time a capacitive sensing system output signal 15, a low pass filtered signal 72 and a bandpass (trigger) signal 80 (generated by the system of FIGS. 3 and 4) as a probe 11 moves towards and then contacts the meniscus of a liquid in a container 14 in presence of two static discharge events. The output signal 15 is a digital signal representation of the sampled peak voltage value developed on the capacitance $C_1$. The low pass filtered signal 72 is a digital signal representation of the low pass filtered output signal 15. The left-hand y-axis of the graph accordingly measures the digitized sampled peak voltage value. The bandpass filtered (trigger) signal 80 is a digital signal representation of the bandpass filtered output signal 15. Since the bandpass filtering operation removes DC offset present in the signal 15, the left-hand y-axis cannot be properly scaled in the illustration to show the signal 80 with the signals 15 and 72 in connection with the same y-axis. Accordingly, the right-hand y-axis is used to measure the digitized sampled and bandpass filtered peak voltage value for signal 80. The x-axis measures time in number of samples, wherein the time between sampling instants could, for example, be 500 μsec. The illustrated time domain is applicable to all three signals 15, 72 and 80.

Figure 7:
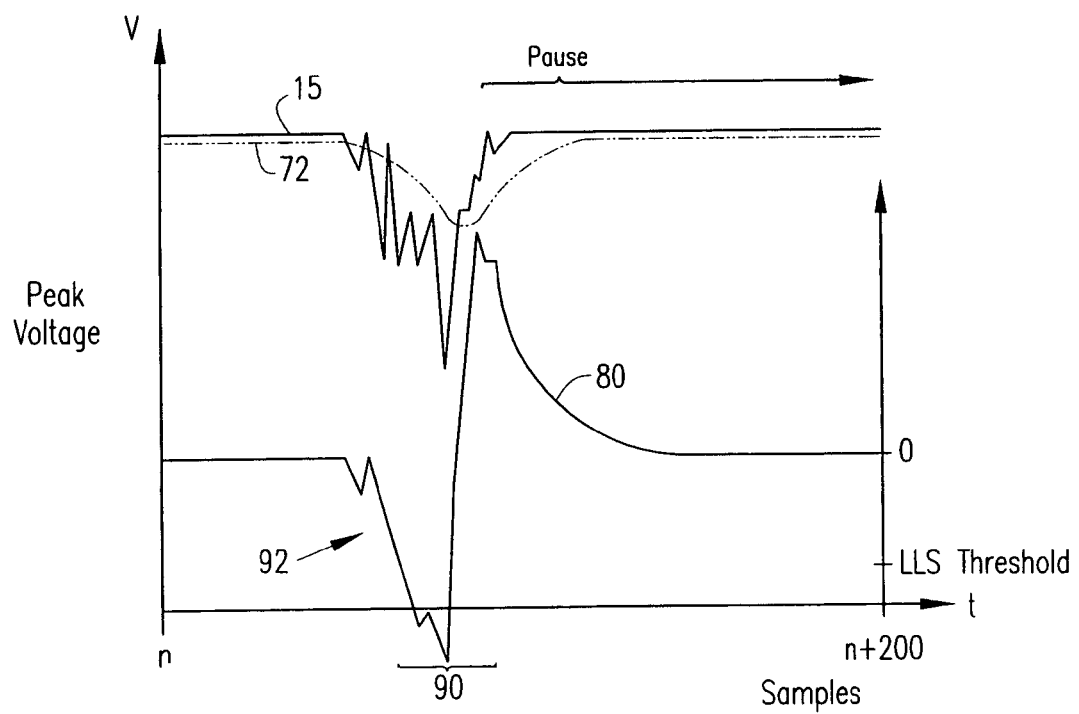
FIG. 7 is a graph showing the signals of FIG. 6 in more detail surrounding one of the static discharge events.

The graph shows the output signal 15 peak voltage value generally rising with time as the probe 11 is moved by the servo-drive 12 into the container 14 closer to the meniscus of the contained fluid. The low pass filtered output signal 72 closely tracks the signal 15 (again, with attenuated high frequency interference effects), but does not include interference components which could distort or perturb the signal 15 and perhaps cause a false positive event detection. At the sampling instance referenced 90 a first static discharge event occurs (see, also, FIG. 7). This injected dynamic interference from the static discharge perturbs the signals 15 and 72 by causing the measured peak voltage at the capacitance $C_1$ to decrease and thus produce a voltage drop. The bandpass filtered trigger signal 80 spikes 92 as a result of the perturbation in the signals 15 and 72. If the magnitude of this spike exceeds the LLS threshold (FIG. 5, 200 and 202), then the debounce state machine 74 of the interference rejection scheme 60 detects an event 208. Otherwise, the perturbation is ignored. In this instance, the spike in signal 80 has surpassed the LLS threshold (in the negative direction) thus indicating that an event has occurred.

It is unknown at this point in time by the system 10' whether this event is noise (interference) or a liquid sense event. To make this determination, the system 10' first causes a pause to z-axis movement of the probe 11, and then the integration process 250 of FIG. 5 is executed to evaluate a number of subsequent sampled values. In effect, this integration process 250 compares value of the low pass filtered signal 72 to a pre-event value over a plurality of sampling points while the probe 11 is stationary. In one embodiment, if a number of sampling point values are found to be below the pre-event value by at least the LLS threshold such that a PASS threshold (214 and 228) is satisfied, the processing scheme considers the event a liquid level sense event. Conversely, if a number of subsequent sampling point values are found within the LLS threshold of the pre-event value such that the FAIL threshold (218 and 236) is satisfied, the processing scheme considers the event a noise/interference event. For the example illustrated in FIGS. 6 and 7, the samples of the signal 72 following the event may drop initially below the pre-event value but thereafter return to and remain stable at approximately the pre-event value. Thus, this event, as is appropriate since it was caused by a static discharge, would be found by the processing scheme to be noise since the loop through path 216 would be taken iteratively to decrement the pass counter and the FAIL threshold comparison would eventually be satisfied. The ramp-up signal 88 would then be issued 242 and probe 11 movement would resume.

A subsequent second static discharge event at reference 94 would be handled by the system 10' in an identical manner as discussed above.

Figure 8:
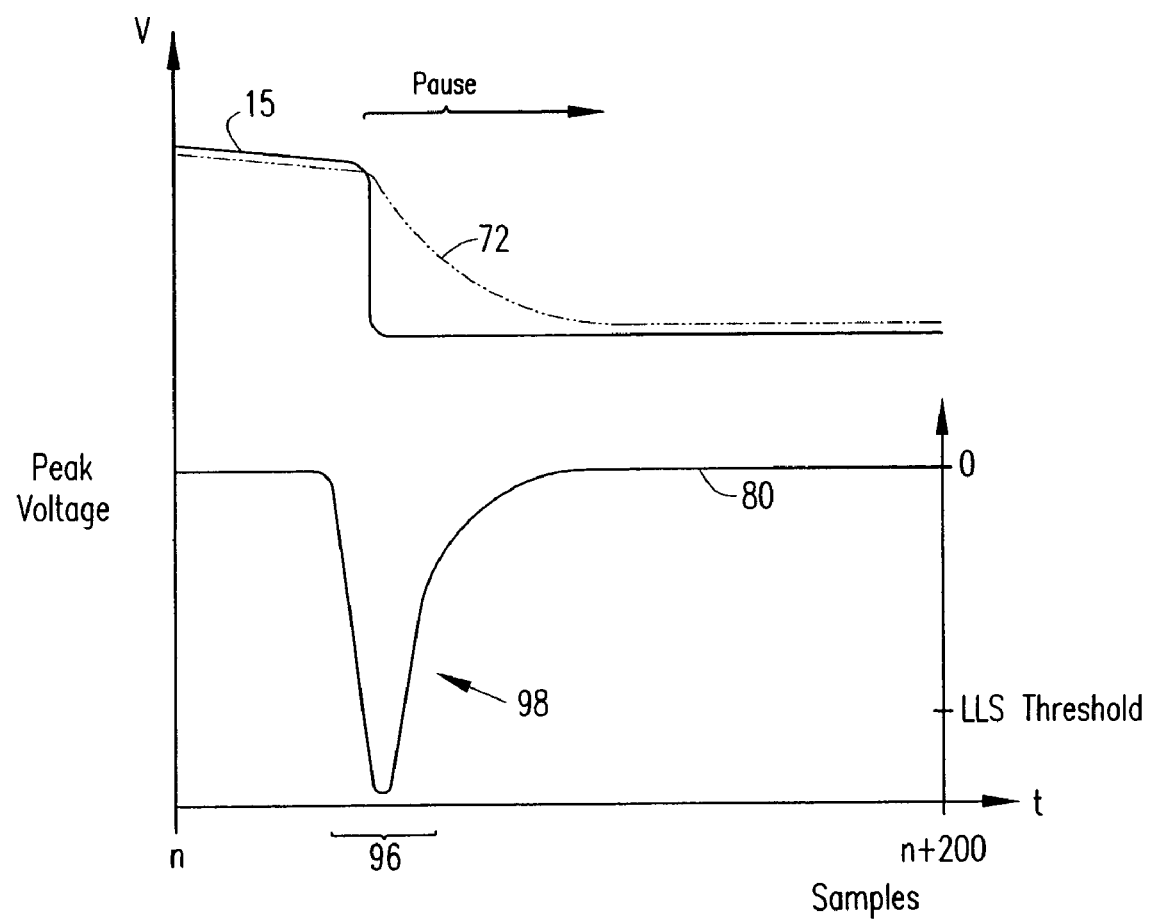
FIG. 8 is a graph showing the signals of FIG. 6 in more detail surrounding the liquid level sensing event.

Following continuation of probe z-axis movement towards the liquid, the graph shows the output signal 15 peak voltage value generally rising with time as the probe 11 is moved by the servo-drive 12 into the container 14 and closer to the meniscus of the contained fluid. The low pass filtered output signal 72 tracks the signal 15. At the sampling instance referenced 96, the probe 11 moves towards and then contacts the meniscus of the liquid in the container 14 (see, also, FIG. 8). The penetration of the liquid meniscus causes a drop in the measured peak voltage at the capacitance $C_1$. The bandpass filtered signal 80 spikes 98 as a result of the voltage drop in the signals 15 and 72. If the magnitude of this spike exceeds the LLS threshold (FIG. 5, 200 and 202), then the debounce state machine 74 of the interference rejection processing scheme 60 detects an event 208. Otherwise, the voltage drop is ignored. In this instance, the spike in signal 80 is below the LLS threshold thus, indicating that an event has occurred.

Again, it is unknown at this point in time by the system 10' whether this event is noise (interference) or a liquid sense event. To make this determination, the system 10' pauses further z-axis movement of the probe 11 and the integration process 250 of FIG. 5 is executed to evaluate a number of subsequent sampled values. In effect, this integration process 250 compares the value of the low pass filtered signal 72 to the pre-event value over a plurality of sampling points while the probe 11 is stationary. If a number of sampling point values are found to be below the pre-event value by at least the LLS threshold such that the PASS threshold 214 and 228 is satisfied, the processing scheme considers the event a liquid level sense event. Conversely, if a number of subsequent sampling point values are found within the LLS threshold of the pre-event value such that the FAIL threshold 218 and 236 is satisfied, the processing scheme considers the event a noise/interference event. For the example illustrated in FIGS. 6 and 8, the subsequent samples of the signal 72 following the event drop below and remain below the pre-event value. Thus, this event, as is appropriate since it was caused by probe 11 penetration into the meniscus, would be found by the processing scheme to be a liquid sense event since the loop through path 212 would be taken iteratively to increment the pass counter and the PASS threshold comparison would eventually be satisfied.

It will accordingly be recognized that operation of the system 10' presented herein reduces the number of LLS false positives (i.e., erroneously sensing liquid before contact is made) and hence increases the reliability of system operation.

The illustrated system thus provides a "trigger" signal that indicates an event and allows for a control to stop probe movement to reduce contamination, a low pass filtered data signal that reduces the intensity of periodic, high frequency EMI, a pausing probe movement which allows a longer LPF time constant (i.e., stronger filtering, improved noise rejection) and for a large portion of the LPF data signal to be analyzed. Pausing probe movement can also allow the tip speed during normal (i.e., noise free) operation to remain relatively high, and can also distribute events in time for event discrimination (e.g., discriminate between closely timed static event and liquid events). Pausing probe movement also allows static to be dissipated so that as the tip continues to search for liquid, less static is encountered. Accordingly, probe movement pausing is allowed to occur multiple times during a liquid level search, so multiple layers of static charge can be discriminated. In cases where a droplet exists on the probe end, the liquid level may still be found accurately since probe movement is paused during the initial level sense, and the liquid surface may wick the droplet away, creating a noise event such that the probe will continue to search for the actual liquid level.

What has thus been described, in one embodiment, are methods and systems in which periodic electromagnetic interference (EMI), pulsed EMI, and static electrical interference are reduced and/or rejected in a capacitive liquid level sensor (LLS) system. Digital filters can reduce periodic EMI and pause probe (and/or sensor) movement when a liquid sense event or noise event occurs. While the probe is paused, the methods and systems can process the filtered LLS data to determine whether a step change in the LLS data has occurred. Such a step change in the LLS data signifies that the probe tip has contacted (or separated from), or moved into and/or out of contact with the liquid. Because noise due to static or EMI is generally pulses of short duration and does not cause a step change in the LLS data, the noise is rejected and the probe is commanded to continue its movement.

Although the primary implementation of the teachings is illustrated with respect to the detection of probe penetration into a meniscus of a fluid within a container, it will be understood that the system and process are equally applicable to the detection of a probe leaving a meniscus. Thus, as used herein, the term "liquid sense" refers to the probe either entering or leaving the liquid within the container. Further, although the illustrated embodiments indicate liquids that are associated with a container, the present methods and systems are not limited to liquids in a container and can be applied to liquids absent in a container, for example, liquids that are present on a surface and held thereon by surface tension.

Although the system 10' is illustrated controlling the operation of a single probe 11, it will be understood by those skilled in the art the system 10', along with the processing scheme 60, is well suited for the control of plural probes.

Although embodiments of the method and apparatus of the present teachings have been illustrated in the accompanying Drawings and described in the foregoing Detailed Description, it will be understood that the teachings are not limited to the embodiments disclosed, but are capable of numerous rearrangements, modifications and substitutions without departing from the spirit of the teachings as set forth and defined by the following claims.

What is claimed is:

1. A system for processing a signal indicative of a capacitance formed between a probe that is controlled to move at least one of into and out of contact with a liquid, and the liquid, the system comprising:
    a low pass filter that operates on the capacitance indicative signal to produce a filtered capacitance indicative signal;
    a high pass filter that operates on the filtered capacitance indicative signal to produce a trigger signal indicative of an event with respect to probe movement; and
    processor instructions operable on the filtered capacitance indicative signal and trigger signal, where the instructions detect occurrence of the event from the trigger signal and pause the movement of the probe in response to a detected event occurrence, and wherein the processor instructions include instructions to process the filtered capacitance indicative signal while the probe movement is paused to determine whether the detected event occurrence is an interference event or a liquid sensing event.

2. The system of claim 1 wherein the processor instructions restart movement of the probe if the detected event occurrence is determined to be an interference event.

3. The system of claim 2 in which the processor instructions restart movement of the probe in a direction that is the same as a direction it was moving prior to pausing the probe movement.

4. A method for processing a signal indicative of a capacitance formed between a probe that is controlled to move at least one of into and out of contact with a liquid, and the liquid, the method comprising:
    low pass filtering the capacitance indicative signal to produce a filtered capacitance indicative signal;
    high pass filtering the filtered capacitance indicative signal to produce a trigger signal indicative of an event with respect to probe movement;
    processing the trigger signal to detect occurrence of the event;
    pausing the movement of the probe in response to a detected event occurrence; and
    processing the filtered capacitance indicative signal while the probe movement is paused to determine whether the detected event occurrence is an interference event or a liquid sensing event.

5. The method of claim 4 further including restarting movement of the probe if the detected event occurrence is determined to be an interference event.

6. The method of claim 5 in which the movement of the probe is restarted in a direction that is the same as a direction it was moving prior to pausing the probe movement.

7. A system for processing a signal indicative of a capacitance formed between a probe that is controlled to move at least one of into and out of contact with a liquid, and the liquid, the system comprising:
    a low pass filter and a high pass filter, wherein one of the low pass filter and the high pass filter provides a filtered capacitance indicative signal from the capacitive indicative signal, and together the low pass filter and the high pass filter provide a trigger signal indicative of an event with respect to probe movement; and
    a processor comprising processor instructions operable on the trigger signal, where the instructions detect occurrence of the event from the trigger signal and pause the movement of the probe in response to a detected event occurrence, and wherein the processor instructions include instructions to process the filtered capacitance indicative signal while the probe movement is paused to determine whether the detected event occurrence is an interference event or a liquid sensing event.

8. The system of claim 7 wherein the processor instructions restart movement of the probe if the detected event occurrence is determined to be an interference event.

9. A method for processing a signal indicative of a capacitance formed between a probe that is controlled to move at least one of into and out of contact with a liquid, and the liquid, the method comprising:
    low pass filtering and high pass filtering the capacitive indicative signal, wherein one of the low pass filter and the high pass filter provides a filtered capacitance indicative signal from the capacitive indicative signal, and together the low pass filtering and the high pass filtering provides a trigger signal indicative of an event with respect to probe movement;

processing the trigger signal to detect occurrence of the event;

pausing the movement of the probe in response to a detected event occurrence; and processing the filtered capacitance indicative signal while the probe movement is paused to determine whether the detected event occurrence is an interference event or a liquid sensing event.

10. The method of claim 9 further including restarting movement of the probe if the detected event occurrence is determined to be an interference event.

11. The system of claim 10 in which the movement of the probe is restarted in a direction that is the same as a direction it was moving prior to pausing the probe movement.

12. A method for processing a signal indicative of a capacitance formed between a probe that is controlled to move at least one of into and out of contact with a liquid, and the liquid, the method comprising:

low pass filtering the capacitance indicative signal to produce a filtered capacitance indicative signal;

high pass filtering the filtered capacitance indicative signal to produce a trigger signal indicative of an event with respect to probe movement;

processing the trigger signal to detect occurrence of the event;

pausing the movement of the probe in response to a detected event occurrence;

processing the filtered capacitance indicative signal while the probe movement is paused to determine whether the detected event occurrence is an interference event or a liquid sensing event;

restarting movement of the probe if the detected event occurrence is determined to be an interference event, wherein the probe movement is restarted in a direction that is the same as a direction in which the probe was moving prior to pausing the probe movement; and not restarting movement of the probe if the detected event occurrence is determined to be a liquid sensing event.

* * * * *